United States Patent [19]

Weichert

[11] 4,331,870
[45] May 25, 1982

[54] APPARATUS FOR X-RAY FLUORESENCE ANALYSIS

[75] Inventor: Norbert Weichert, Ettlingen, Fed. Rep. of Germany

[73] Assignee: Siemens Aktiengesellschaft, Munich, Fed. Rep. of Germany

[21] Appl. No.: 161,277

[22] Filed: Jun. 19, 1980

[30] Foreign Application Priority Data

Jun. 25, 1979 [DE] Fed. Rep. of Germany ....... 2925593

[51] Int. Cl.³ .............................................. G01N 23/20
[52] U.S. Cl. .................................................... 250/280
[58] Field of Search ............................... 250/280, 272

[56] References Cited

U.S. PATENT DOCUMENTS 3,079,501  2/1963  Birks, Jr. ............................... 250/280
3,663,812  5/1972  Koenig et al. ......................... 250/280
4,131,794 12/1978  Bruninx ................................ 250/280

Primary Examiner—Alfred E. Smith
Assistant Examiner—T. N. Grigsby
Attorney, Agent, or Firm—Kenyon & Kenyon

[57] ABSTRACT

In apparatus for x-ray fluorescence analysis in which x-ray fluorescence radiation is excited in a specimen, in order to obtain simultaneous coverage of fluorescence radiation of different wavelengths even from inhomogeneous specimens, the source for the radiation to be analyzed is made point shaped or line shaped, the source is located at the focus of a parabolically curved analyzer crystal, the lattice planes of which are parallel to its surface, and a position sensitive detector is arranged with its axis perpendicular to the parabola axis of the parabolic analyzer crystal, opposite the analyzer crystal.

6 Claims, 1 Drawing Figure

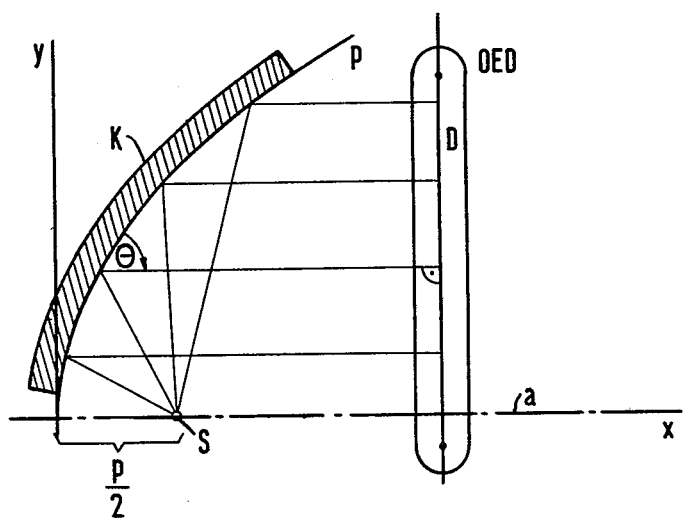

APPARATUS FOR X-RAY FLUORESENCE ANALYSIS

BACKGROUND OF THE INVENTION

This invention relates to apparatus for x-ray fluorescence analysis, in general and more particularly to such apparatus for examining both homogeneous and inhomogeneous samples.

Apparatus for x-ray fluorescence analysis comprising means for exciting x-ray fluorescence radiation in a sample, an analyzer crystal and a position-sensitive detector is described in a research paper "X-ray fluorescence analysis by means of crystal dispersion and a position-sensitive counter" in "Spectrochimica Acta," vol. 31B (1976), pages 221 to 223. The apparatus is based on a simple x-ray spectrograph first described by Seemann in 1916, which, however, still used photo-sensitive film. The fluorescent radiation emitted by a specimen surface falls into a slit formed between a narrow strip of an analyzer crystal and a lamination opposite the strip. It is refracted in the analyzer crystal according to Bragg's law and falls on the other side of the slit on different points of a position sensitive detector, depending on the wavelength. The radiation of each wavelength stems from another narrowly defined region of the specimen surface, so that this known apparatus can be used directly only for homogeneous samples.

It is the object of the present invention to provide apparatus of this nature with which inhomogeneous samples can also be examined.

SUMMARY OF THE INVENTION

According to the present invention, this problem is solved in apparatus of the type described above by providing means for making the source for the radiation to be analyzed approximately point shaped or line shaped; by providing the focus of the parabolically curved analyzer crystal, the lattice planes of which are parallel to its surface, as the location for the source; and by arranging the axis of the position sensitive detector perpendicular to the parabola axis of the parabolic analyzer crystal.

With the new apparatus, all fluorescent radiation of different wavelengths emanating from a region on the surface of a specimen can be covered. Radiation of different wavelengths does not stem here from different points on the specimen surface, so that even inhomogeneous samples can be examined directly.

The means for shaping the source are advantageously a point or slit aperture, behind which a sample excited by primary radiation is arranged.

In another embodiment of the present invention, the means for shaping the source can be combined with the means for exciting the source. This refers to a point or slit aperture for the exciting primary radiation or a focussed electron beam with a point shaped or line shaped cross section. Also, the parabolically curved analyzer crystal can be replaced in approximation by individual, bent crystal sections, which are not parabolic themselves but the average curvatures of which agree approximately with the curvatures of the parabola sections replaced by them.

Advantageously, the analyzer crystal should also extend in a direction perpendicular to the plane of the parabola.

An optically particularly powerful arrangement can be obtained with a double curvature crystal if the crystal is made with symmetry of rotation with respect to the detector axis, for instance a counter tube wire.

All rays refracted by the analyzer crystal are parallel to the axis of the parabola and always strike the axis of the position sensitive detector, for instance the wire of a counter tube, at right angles. This promotes good spatial resolution.

BRIEF DESCRIPTION OF THE DRAWING

The single FIGURE is a schematized cross section through the arrangement of an analyzer crystal and detector according to the present invention.

DETAILED DESCRIPTION OF THE INVENTION

In the figure, the means for exciting the x-ray fluorescence radiation have been omitted for the sake of clarity. They can be arranged at places where they do not interfere with the ray path of the x-ray fluorescence radiation, for instance, in the vicinity of the apex of the parabola. The surface of the specimen can be aligned, for instance, parallel to the chord of the parabola section covered by the analyzer crystal.

In the figure, this parabola section P, the apex of which is located at the origin of an orthogonal coordinate system, with an x-axis and a y-axis. Part of the parabola is covered by a parabolically curved crystal K, which also extends perpendicular to the plane of the drawing. A source S, e.g., a sample being excited, for x-ray fluorescence radiation is located at the focus of the parabola at a distance p/2 from the apex. Perpendicular to the x-axis, which at the same time, forms the axis a of the parabola, i.e., parallel to the y-axis, is located the spatial axis of a position sensitive detector OED, which is formed by a counter tube, the wire D of which is located on the axis of the detector OED. To the extent that they meet the Bragg condition $z \cdot \lambda = 2d \sin \theta$, all rays emanating from the source S at the focus are refracted by the crystal parallel to the axis of the parabola and strike the counting tube wire at a right angle. The angle $\theta$ is the angle between a reflected ray and the tangent to the parabola at the point of incidence of the incident ray; d is the distance of the net planes and $\lambda$ is the wavelength of the x-ray fluorescence radiation. The equation for the parabola P can be written in the form $y^2 = 2px$. Then we have for the tangent of the angle $\theta$: $\tan \theta = dy/dx = p/y$ (because $y^2 = 2px$, we have $2yy' = 2p$ and $y' = p/y$). By converting the tan into a sine function, one obtains:

$$\sin \theta = \frac{\tan \theta}{\sqrt{1 + \tan^2 \theta}} = \frac{p}{y} \cdot \frac{1}{\sqrt{1 + (p/y)^2}} = \left(\frac{y^2}{p^2} \times 1\right)^{-\frac{1}{2}}$$

and, substituted into the Bragg relation:

$$z \cdot \lambda = \frac{2d}{\sqrt{1 + (y/p)^2}}.$$

This, then, is the dispersion equation for the dependence of the wavelength $\lambda$ on the wire position y.

What is claimed is:

1. In apparatus for x-ray fluorescence analysis, comprising means for exciting x-ray fluorescence radiation in a specimen to provide a source of radiation, an analyzer crystal and a position sensitive detector, the improvement comprising:

(a) means for shaping the source for the radiation to be analyzed to be approximately point shaped or line shaped;

(b) the analyzer crystal being a parabolically curved analyzer crystal, the lattice planes of which are parallel to its surface, the source located at its focus; and (c) the position sensitive detector arranged with its axis perpendicular to the axis of the parabola of the parabolic analyzer crystal opposite said crystal.

2. The improvement according to claim 1, wherein said means for shaping the source comprise a point or slit aperture, behind which a specimen irradiated by a primary radiation is arranged.

3. The improvement according to claim 1, wherein said means for shaping the source are combined with the means for exciting the source.

4. The improvement according to claim 1 wherein said parabolically bent analyzer crystal is approximated by individual, not parabolically bent, crystal sections, the average curvatures of which approximately agree with the curvatures of the sections of the parabola which they represent.

5. The improvement according to claim 1, wherein said analyzer crystal also extends in a direction perpendicular in the plane of the parabola.

6. The improvement according to claim 5, wherein said analyzer crystal comprises a double curvature analyzer crystal which has rotational symmetry with respect to the detector axis.

* * * * *